United States Patent
Minton et al.

(10) Patent No.: US 11,638,689 B2
(45) Date of Patent: *May 2, 2023

(54) DEEP TOPICAL SYSTEMIC NITRIC OXIDE THERAPY APPARATUS AND METHOD

(71) Applicant: SYK Technologies LLC, Newport Beach, CA (US)

(72) Inventors: Christian S. Minton, Provo, UT (US); Stephen D. Minton, Provo, UT (US); J. W. Randolph Miller, Orem, UT (US)

(73) Assignee: SYK TECHNOLOGIES, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,042

(22) Filed: May 26, 2022

(65) Prior Publication Data
US 2022/0354781 A1 Nov. 10, 2022

Related U.S. Application Data

(60) Continuation of application No. 17/082,709, filed on Oct. 28, 2020, which is a division of application No. 15/492,528, filed on Apr. 20, 2017, now Pat. No. 10,828,249, which is a division of application No. 14/274,419, filed on May 9, 2014, now Pat. No. 10,517,817.

(60) Provisional application No. 61/990,591, filed on May 8, 2014, provisional application No. 61/888,415, filed on Oct. 8, 2013, provisional application No. 61/821,443, filed on May 9, 2013.

(51) Int. Cl.
A61K 9/00 (2006.01)
A61K 33/00 (2006.01)
A61K 47/02 (2006.01)

(52) U.S. Cl.
CPC ............ *A61K 9/0014* (2013.01); *A61K 33/00* (2013.01); *A61K 47/02* (2013.01)

(58) Field of Classification Search
CPC .... A61K 31/194; A61K 33/00; A61K 9/0014; A61K 47/12; B05C 9/06
See application file for complete search history.

(56) References Cited

U.S. PATENT DOCUMENTS

| | | | |
|---|---|---|---|
| 2,310,907 A | 2/1943 | McMillan | |
| 3,485,915 A | 12/1969 | Gerstein et al. | |
| 3,682,171 A | 8/1972 | Dali et al. | |
| 4,142,508 A | 3/1979 | Watson | |
| 4,287,040 A | 9/1981 | Alamaro | |
| 4,774,069 A | 9/1988 | Handley | |
| 4,778,450 A | 10/1988 | Kamen | |
| 4,943,066 A | 7/1990 | Lathim et al. | |
| 5,045,292 A | 9/1991 | Ruegg et al. | |
| 5,047,166 A | 9/1991 | Weil | |
| 5,063,050 A | 11/1991 | Verdon et al. | |
| 5,427,797 A | 6/1995 | Frostell et al. | |
| 5,485,827 A | 1/1996 | Zapol et al. | |
| 5,560,919 A | 10/1996 | Morikawa et al. | |
| 5,570,683 A | 11/1996 | Zapol | |
| 5,648,101 A | 7/1997 | Tawashi | |
| 5,692,495 A | 12/1997 | Sheu | |
| 5,713,349 A | 2/1998 | Keaney | |
| 5,813,932 A | 9/1998 | Grafton | |
| 5,816,704 A | 10/1998 | Campbell et al. | |
| 5,823,180 A | 10/1998 | Zapol | |
| 5,839,433 A | 11/1998 | Higenbottam | |
| 5,869,539 A | 2/1999 | Garfield et al. | |
| 5,873,359 A | 2/1999 | Zapol et al. | |
| 5,891,472 A | 4/1999 | Russell | |
| 5,900,433 A | 5/1999 | Igo et al. | |
| 5,915,378 A | 6/1999 | Lloyd | |
| 6,000,403 A | 12/1999 | Cantwell | |
| 6,001,279 A | 12/1999 | Payzant et al. | |
| 6,019,100 A | 2/2000 | Alving et al. | |
| 6,063,407 A | 5/2000 | Zapol et al. | |
| 6,089,229 A | 7/2000 | Bathe et al. | |
| 6,103,275 A | 8/2000 | Seitz et al. | |
| 6,131,572 A | 10/2000 | Heinonen | |
| 6,142,147 A | 11/2000 | Head et al. | |
| 6,149,606 A | 11/2000 | Alving et al. | |
| 6,432,077 B1 | 8/2002 | Stenzler | |
| 6,458,109 B1 | 10/2002 | Henley et al. | |
| 6,572,594 B2 | 6/2003 | Satterfield et al. | |

(Continued)

FOREIGN PATENT DOCUMENTS

CA 3142109 A1 12/2020
EP 2575829 4/2013

(Continued)

OTHER PUBLICATIONS

Burleigh, et al., Free Radical Biology and Medicine, May 2018, vol. 120, pp. 80-88. Year: 2018.
"Guidance for Industry and for FDA Reviews—Guidance Document for Premarket Notification Submissions for Nitric Oxide Delivery Apparatus, Nitric Oxide Analyzer and Nitrogen Dioxide Analyzer", U.S. Food and Drug Administration Center for Devices and Radiological Health, Jan. 24, 2000, Updated Mar. 29, 2007, pp. 1-34, hhtp://www.fda.gov/cdrh/ode/1157.html.

(Continued)

*Primary Examiner* — Mark V Stevens
(74) *Attorney, Agent, or Firm* — Honigman LLP; Heidi Berven

(57) ABSTRACT

A topical mixture that produces nitric oxide and a method for using the topical mixture to increase the vasodilation of a bloodstream via transdermal absorption of the nitric oxide. The nitric oxide can then affect subcutaneous tissues. The systemic vasodilation of a mammal may be increased via a topical application of an appropriate nitric oxide producing substance.

21 Claims, 3 Drawing Sheets

(56) References Cited

U.S. PATENT DOCUMENTS

| | | |
|---|---|---|
| 6,581,599 B1 | 6/2003 | Stenzler |
| 6,601,580 B1 | 8/2003 | Bloch et al. |
| 6,612,306 B1 | 9/2003 | Mault |
| 6,670,323 B1 | 12/2003 | Looker et al. |
| 6,689,810 B2 | 2/2004 | Martin |
| 6,749,834 B2 | 6/2004 | Fein et al. |
| 6,758,214 B2 | 7/2004 | Fine et al. |
| 6,763,832 B1 | 7/2004 | Kirsch et al. |
| 6,786,217 B2 | 9/2004 | Stenzler |
| 6,793,644 B2 | 9/2004 | Stenzler |
| 7,017,573 B1 | 3/2006 | Rasor et al. |
| 7,025,869 B2 | 4/2006 | Fine et al. |
| 7,040,313 B2 | 5/2006 | Fine et al. |
| 7,045,152 B2 | 5/2006 | Stamler |
| 7,048,951 B1 | 5/2006 | Seitz et al. |
| 7,066,356 B2 | 6/2006 | Schuman et al. |
| 7,122,018 B2 | 10/2006 | Stenzler et al. |
| 7,220,393 B2 | 5/2007 | Miller et al. |
| 7,381,377 B2 | 6/2008 | Ross |
| 7,914,743 B2 | 3/2011 | Fine et al. |
| 7,939,045 B2 | 5/2011 | Miller et al. |
| 8,066,904 B2 | 11/2011 | Fine et al. |
| 8,221,800 B2 | 7/2012 | Fine et al. |
| 8,434,475 B2 | 5/2013 | Miller et al. |
| 8,518,457 B2 | 8/2013 | Miller et al. |
| 8,574,531 B2 | 11/2013 | Miller et al. |
| 8,668,937 B2 | 3/2014 | Perricone et al. |
| 8,685,467 B2 | 4/2014 | Miller et al. |
| 8,720,436 B2 | 5/2014 | Jones |
| 8,770,440 B2 | 7/2014 | Lin |
| 8,980,331 B2 | 3/2015 | Chen et al. |
| 9,107,860 B2 | 8/2015 | Miller et al. |
| 9,138,707 B2 | 9/2015 | Miller et al. |
| 9,302,238 B2 | 4/2016 | Miller et al. |
| 9,486,477 B2 | 11/2016 | Miller et al. |
| 9,629,871 B2 | 4/2017 | Miller et al. |
| 9,649,467 B2 | 5/2017 | Miller et al. |
| 9,717,875 B2 | 8/2017 | Miller et al. |
| 9,730,956 B2 | 8/2017 | Stenzler et al. |
| 9,744,510 B2 | 8/2017 | Miller et al. |
| 9,877,986 B2 | 1/2018 | Miller et al. |
| 10,052,348 B2 | 8/2018 | Miller et al. |
| 10,517,817 B2 | 12/2019 | Minton et al. |
| 10,543,336 B2 | 1/2020 | Miller et al. |
| 10,751,364 B2 | 8/2020 | Miller et al. |
| 10,828,249 B2 | 11/2020 | Minton et al. |
| 10,905,712 B2 | 2/2021 | Stenzler et al. |
| 11,304,972 B2 | 4/2022 | Miller et al. |
| 2001/0037810 A1 | 11/2001 | Fine et al. |
| 2002/0110590 A1 | 8/2002 | Shaked et al. |
| 2002/0132730 A1 | 9/2002 | Hwang et al. |
| 2002/0182162 A1 | 12/2002 | Shahinpoor et al. |
| 2003/0062043 A1 | 4/2003 | Fine et al. |
| 2003/0064028 A1 | 4/2003 | Fine et al. |
| 2003/0064115 A1 | 4/2003 | Fine et al. |
| 2004/0002438 A1 | 1/2004 | Hawkins et al. |
| 2004/0013747 A1 | 1/2004 | Tucker et al. |
| 2004/0163647 A1 | 8/2004 | Figley |
| 2004/0197274 A1 | 10/2004 | Fein et al. |
| 2005/0214193 A1 | 9/2005 | D'Ottone |
| 2006/0032495 A1 | 2/2006 | Fernandez |
| 2006/0172018 A1 | 8/2006 | Fine et al. |
| 2007/0059351 A1 | 3/2007 | Murrell et al. |
| 2007/0154569 A1* | 7/2007 | Gladwin .................... A61P 7/04 424/718 |
| 2007/0190184 A1 | 8/2007 | Montgomery et al. |
| 2007/0239107 A1 | 10/2007 | Lundberg et al. |
| 2008/0045909 A1* | 2/2008 | Fossel .................... A61Q 19/08 604/290 |
| 2008/0173311 A1 | 7/2008 | Miller et al. |
| 2008/0317679 A1 | 12/2008 | Tamarkin et al. |
| 2010/0018526 A1* | 1/2010 | Miller .................... B01D 53/22 128/203.12 |
| 2010/0089392 A1 | 4/2010 | Fine et al. |
| 2010/0104667 A1 | 4/2010 | Fine et al. |
| 2011/0117187 A1* | 5/2011 | Stock .................... A61P 31/00 424/59 |
| 2011/0240020 A1 | 10/2011 | Fine et al. |
| 2011/0311653 A1 | 12/2011 | Kevil et al. |
| 2012/0048891 A1 | 3/2012 | Hagleitner |
| 2012/0093948 A1 | 4/2012 | Fine et al. |
| 2013/0200109 A1 | 8/2013 | Yang et al. |
| 2013/0330244 A1* | 12/2013 | Balaban .................... A61P 15/00 422/236 |
| 2014/0056957 A1 | 2/2014 | Chen et al. |
| 2014/0251787 A1 | 9/2014 | Montgomery et al. |
| 2014/0275857 A1 | 9/2014 | Toth |
| 2014/0296773 A1 | 10/2014 | Bulent et al. |
| 2015/0328430 A1 | 11/2015 | Miller et al. |
| 2021/0145732 A1 | 5/2021 | Minton et al. |
| 2022/0040224 A1 | 2/2022 | Miller et al. |
| 2022/0054536 A1 | 2/2022 | Miller et al. |

FOREIGN PATENT DOCUMENTS

| | | |
|---|---|---|
| JP | 61-171998 | 8/1986 |
| JP | 63-187196 | 8/1988 |
| WO | WO 02/20026 | 3/2002 |
| WO | WO 2006/110923 | 10/2006 |
| WO | WO 2007/057763 | 5/2007 |
| WO | WO 2008/110872 | 9/2008 |
| WO | WO 2008/116925 | 10/2008 |
| WO | WO 2013/085784 | 6/2013 |
| WO | WO 2013/119642 | 8/2013 |
| WO | WO 2014/031491 | 2/2014 |
| WO | WO 2017/132275 | 8/2017 |
| WO | WO 2020/245573 | 12/2020 |
| WO | WO 2021/214439 | 4/2021 |
| WO | WO 2021/214440 | 4/2021 |

OTHER PUBLICATIONS

Gupta, et al., Journal of Food Science Technology, 2015, vol. 52, pp. 676-684. Year: 2015.

Material Safety Data Sheet, Soda lime MSDS, ScienceLab.com, created Oct. 9, 2005, in 6 pages.

Oliveira-Paula, et al., Nitric Oxide, Apr. 2019, vol. 85, pp. 35-43. Year: 2019.

Ray, James D., Ogg Jr., Richard A. "A New Method of Preparing Nitric Oxide" Department of Chemistry, Stanford University, as early as Jul. 25, 1956.

Snow et al., "Size Reduction and Size Enlargement," 1997, Perry's Chemical Engineers Handbook, McGraw-Hill, Section 20, pp. 20-21-20-89.

"Viasys Healthcare Inc. and INO Therapeutics, LLC Reach Settlement" Business Wire, May 14, 2004, pp. 1-2, Conshohocken, PA and Clinton, N.J., http://findarticles.com/p/articlesmi_m0EIN/is_ 2004_May_14/ai_ n6028801.

Williams, Steven C., "FDA Compliant, Food Grade and Food Safe", dated Jun. 11, 2020 in 3 pages.

Www.thefreedictionary.com/sieve, Mar. 10, 2015, in 1 page.

Www.dictionary/reference.com/browse/integrate, Mar. 10, 2015, in 1 page.

* cited by examiner

Study Design

| Study Number | Site of Gel Application | Gel Number | Amount (grams) Applied |
|---|---|---|---|
| 1 | R leg – 6" above the and below knee | A | 15 |
| 2 | R leg – mid-thigh to ankle | A | 15 |
| 3 | Chest – 12" square | A | 15 |
| 4 | Chest – entire | A | 15 |
| 5 | R leg – mid-thigh to just above ankle | A | 30 |
| 6 | R and L leg – mid-thigh to just above ankle | B | 30 (15 ea) |
| 7 | R and L leg – mid-thigh to just above ankle | A | 30 (15 ea) |
| 8 | R and L leg – mid-thigh to just above ankle (keep wet) | A | 30 (15 ea) |
| 9 | R leg calf – 12" circumferential (covered by aluminum foil) | C | 30 |
| 10 | R and L calf and thigh both legs – 12" circumferential on each | C | 60 (30 ea) |
| 11 | L leg calf – 12" circumferential | C | 15 |
| 12 | L leg calf – 12" circumferential | C | 30 |
| 13 | R and L leg calf 12" circumferential | C | 30 (15 ea) |
| 14 | R and L leg calf 12" circumferential | C | 30 (15 ea) |
| 15 | R and L leg calf 12" circumferential | C | 30 (15 ea) |
| 16 | R and L leg calf 12" circumferential | C | 30 (15 ea) |
| 17 | R leg thigh and R leg calf 12" circumferential each | C | 30 (15 ea) |
| 18 | R and L leg thigh and calf 12" circumferential each | C | 60 (30 ea) |

Figure 1

Peripheral Perfusion Index (PI) Change after Topical Acidified Nitrite Application

| Study | Highest Baseline PI | Highest Post Acidified Nitrite PI | % PI Change |
|---|---|---|---|
| 1 | 9.6 | 11.4 | +18.75 |
| 2 | 10.6 | 11.8 | +11.3 |
| 3 | 6.3 | 10.5 | +68.9 |
| 4 | 6.1 | 8.5 | +39.3 |
| 5 | 7.6 | 8.5 | +11.8 |
| 6 | 4.9 | 8.7 | +77.6 |
| 7 | 6.5 | 7.5 | +15.4 |
| 8 | 6.3 | 9.3 | +47.6 |

Average PI increase in Gels A & B   +36.3%

| Study | Highest Baseline PI | Highest Post Acidified Nitrite PI | % PI Change |
|---|---|---|---|
| 9 | 0.8 | 4.5 | +462.5 |
| 10 | 0.2 | 0.5 | +150.0 |
| 11 | 4.4 | 7.0 | +59.0 |
| 12 | 2.3 | 5.1 | +121.7 |
| 13 | 1.7 | 6.0 | +252.9 |
| 14 | 2.0 | 7.0 | +250.0 |
| 15 | 3.1 | 6.0 | +93.5 |
| 16 | 3.4 | 6.2 | +82.4 |
| 17 | 6.0 | 8.2 | +36.7 |
| 18 | 4.6 | 7.5 | +66.7 |

Average PI increase in Gels C   +157.6%

Figure 2

DEEP TOPICAL SYSTEMIC NITRIC OXIDE THERAPY APPARATUS AND METHOD

RELATED APPLICATIONS

This patent application is a continuation of U.S. patent application Ser. No. 17/082,709, filed Oct. 28, 2020, which is a divisional of U.S. patent application Ser. No. 15/492,528, filed Apr. 20, 2017, issued as U.S. Pat. No. 10,828,249 on Nov. 10, 2020; which is a divisional of U.S. patent application Ser. No. 14/274,419, filed May 9, 2014, issued as U.S. Pat. No. 10,517,817 on Dec. 31, 2019; which claims the benefit of U.S. Provisional Patent Application Ser. No. 61/821,443, filed May 9, 2013; U.S. Provisional Patent Application Ser. No. 61/888,415, filed Oct. 8, 2013; and U.S. Provisional Patent Application Ser. No. 61/990,591, filed May 8, 2014, which are hereby incorporated by reference in their entireties.

BACKGROUND

Field of the Invention

This invention relates to generation of nitric oxide (NO), and more particularly, topical application treatments providing nitric oxide as a vasodilator, including transdermal penetration of nitric oxide to deep tissues and blood vessels resulting in vasodilation.

Description of the Related Art

The discovery of the nitric oxide effect in live tissues garnered a Nobel prize. Much of the work in determining the mechanisms for implementing and the effects of nitric oxide administration are reported in literature including papers, advertising, catalogs, and patents.

Much of the work deals with introduction of substances that provide a nitric oxide effect in the body. Other applications involve production and use of nitric oxide to sterilize a variety of surfaces, including a person's skin. As an example, U.S. Pat. No. 8,501,090 discloses production and use of nitric oxide for sterilization purposes, which patent is hereby incorporated by reference in its entirety. Still other applications may involve topical preparations introducing nitric oxide. Still other applications rely on bottled nitric oxide gas. Introduction of nitric oxide to the human body has traditionally been expensive and sometimes difficult to achieve or substantiate.

The therapies, compositions, and preparations for promoting nitric oxide production in the body can be sufficiently expensive to inhibit more widespread use of such therapies, and can lose effectiveness. For example, L-arginine supplements can increase the main precursor for endothelial nitric oxide synthase to produce nitric oxide, which can improve vascular reactivity and functional capacity in the short term, but in the long term can result in no increase in endothelial nitric oxide synthase or nitric oxide, which can decrease vascular reactivity and functional capacity. Nitric oxide donors (systemic nitrovasodilators) can help preserve endothelial function and increase nitric oxide, but a tolerance can be developed, including generating oxidative stress causing further endothelial dysfunction.

What is needed is a comparatively inexpensive mechanism for introducing nitric oxide in a single dosage over an extended period of time. Also, what is needed is a simple, topical application method to promote transdermal absorption of nitric oxide subcutaneously, into deeper tissues of the body, and increase vasodilation. Also, what is needed is a simple, topical application method to promote transdermal absorption of nitric oxide in order to gain numerous other benefits from such nitric oxide absorption in subcutaneous tissues.

Topical uses of nitric oxide producing gels and mediums have included surface uses and applications of such gels and mediums, including anti-septic, sterilization, and wound healing. What is needed is a topical use directed toward transdermal, sub-cutaneous absorption of nitric oxide through healthy skin into the deeper, subcutaneous tissues of the body to promote vasodilation, as well as other benefits from nitric oxide, including but not limited to, anti-inflammatory, antiseptic, microbicide, biofilm dispersal, and analgesic.

SUMMARY OF THE INVENTION

In accordance with the foregoing, certain embodiments of an apparatus and method in accordance with the invention provide a system for generating nitric oxide (NO) having two compounds, typically disposed in separate carriers. The two compounds are separated from one another prior to administration. In order to administer the nitric oxide, reactants are mixed with one another, beginning a reaction releasing nitric oxide. The resultant mixture is applied to the skin so the nitric oxide can be absorbed transdermally into the bloodstream and promote vasodilation of subcutaneous tissues.

In certain embodiments, a topical mixture may include a first medium and a second medium. The first medium may include a nitrite salt capable of providing nitric oxide upon reaction with an acid or reducing agent, for example, the nitrite salt may be sodium nitrite, potassium nitrite, or the like. The second medium may include an acid or reducing agent for reacting with the nitrite salt, for example, the acid or reducing agent may be citric acid, ascorbic acid, phytic acid, acetic acid, formic acid, lactic acid, or the like. The mixture of the first medium and the second medium may initiate production of nitric oxide.

The mixture may also include enough reactants to produce an effective amount of nitric oxide sufficient to increase vasodilation, systemic vasodilation, and nitric oxide levels in a mammal's bloodstream via transdermal, subcutaneous absorption.

In certain embodiments, a method for increasing nitric oxide levels in the bloodstream via transdermal, subcutaneous absorption may include providing a mammal with an epidermal or skin surface, wherein the mammal also has an initial amount of nitric oxide in its bloodstream and an initial systemic vasodilation of the vascular system. Then, a topical mixture that may include a first medium and a second medium is applied to the skin of the mammal. The first medium may include a nitrite salt capable of providing nitric oxide upon reaction with an acid or reducing agent, for example, the nitrite salt may be sodium nitrite, potassium nitrite, or the like. The second medium may include an acid or reducing agent for reacting with the nitrite salt, for example, the acid or reducing agent may be citric acid, ascorbic acid, phytic acid, acetic acid, formic acid, lactic acid, or the like. The mixture of the first medium and the second medium may initiate production of nitric oxide. Thus, the amount of nitric oxide in the bloodstream of the mammal is increased and the systemic vasodilation of its vascular system is increased.

In certain embodiments, the epidermal surface or skin of the mammal may be healthy skin. Also, the epidermal surface of the skin of the mammal may include acne. Also, the epidermal surface of the skin of the mammal may include a biofilm. Also, the skin may be covered with a barrier, cover, or bandage after application of the nitric oxide production mixture.

In certain embodiments, the mixture of reactants may include a buffer concentration that is included to prolong the production of nitric oxide, for example, a salt buffer of the like. A salt like sodium chloride, calcium chloride, or the like, may be added to the first medium, second medium, or both in a sufficient amount to inhibit or slow the reaction between the nitrite salt and the reducing agent.

Also, the mixture of reactants may include thickening agents to increase the viscosity of the mixture, or the viscosity of one or both of the underlying, initial mediums, to prolong the production of nitric oxide, for example, hydroxyethyl cellulose, methyl cellulose, hydroxypropyl methylcellulose, or the like.

In accordance with the present invention, many ailments or diseases may be treated by transdermal, topical mixture applications producing nitric oxide, including without limitation, peripheral artery disease, hypertension, diabetes, atherosclerosis, acne, inflammation, tendonitis, biofilms, and the like.

In certain embodiments, a method for increasing vasodilation in a mammal via transdermal, sub-cutaneous absorption of nitric oxide may include providing a mammal with an epidermal or skin surface, wherein the mammal also has an initial level of vasodilation, or systemic vasodilation, in its vascular system. Then, a topical mixture that may include a first medium and a second medium is applied to the skin of the mammal. The first medium may include a nitrite salt capable of providing nitric oxide upon reaction with an acid or reducing agent, for example, the nitrite salt may be sodium nitrite, potassium nitrite, or the like. The second medium may include an acid or reducing agent for reacting with the nitrite salt, for example, the acid or reducing agent may be citric acid, ascorbic acid, phytic acid, acetic acid, formic acid, lactic acid, or the like. The mixture of the first medium and the second medium may initiate production of nitric oxide. Thus, the systemic vasodilation of the mammal is increased after transdermal absorption of nitric oxide.

Certain embodiments of an apparatus and method in accordance with the invention provide a topical medium that produces nitric oxide and provides a therapeutic concentration of nitric oxide delivered to a surface. Nitric oxide may thus be introduced to the skin, or a wound, of a subject in a controlled manner. Nitric oxide amounts may be engineered to deliver a therapeutically effective amount on the order of from comparatively low hundreds (e.g., 100-500) of parts per million, up to thousands of parts per million (ppm). For example, sufficient nitric oxide may be presented through topical application to provide approximately five hundred parts per million to the surface of a subject's skin, and up to 2500 ppm.

One embodiment of an apparatus and method in accordance with the present invention may rely on equal amounts of a nitrite medium and an acidified medium formulated to provide a burst of nitric oxide, as well as a continuous amount of nitric oxide over a period of time.

One embodiment of an apparatus and method in accordance with the present invention may provide a therapeutically effective amount of nitric oxide from a gel medium, which provides a therapeutically effective dose of nitric oxide over a potentially shorter length of time, from approximately ten to thirty minutes, and potentially up to about 3 hours. The reaction may begin upon combination of the nitrite medium and an acidified gel medium.

One embodiment of an apparatus and method in accordance with the present invention may provide a therapeutically effective amount of nitric oxide from a lotion medium, which provides a therapeutically effective dose of nitric oxide over a potentially longer length of time, from about one hour up to about 6 hours. Reactants may include potassium nitrite, sodium nitrite or the like. The reaction may begin upon combination of the nitrite medium and an acidified medium.

One embodiment of an apparatus and method in accordance with the present invention may provide a therapeutically effective amount of nitric oxide from a serum medium, which provides a therapeutically effective dose of nitric oxide over limited time, from about initial application to thirty minutes or sixty minutes. Reactants may include potassium nitrite, sodium nitrite or the like. The reaction may begin upon combination of the nitrite serum medium and the acidified serum medium.

One embodiment of an apparatus and method in accordance with the present invention may provide a therapeutically effective amount of nitric oxide from a mud (facial mud) medium, which provides a therapeutically effective dose of nitric oxide over limited time, from about initial application from about one hour to about three hours. Reactants may include potassium nitrite, sodium nitrite or the like. The reaction may begin upon combination of the nitrite mud medium and the acidified mud medium.

One embodiment of an apparatus and method in accordance with the present invention may provide a therapeutically effective amount of nitric oxide from a powder medium. The reaction may begin upon combination of the nitrite powder medium and the acidified powder medium being placed in a water bath. A water bath may provide a therapeutically effective dose of nitric oxide over limited time, from about initial application to thirty minutes. Reactants may include potassium nitrite, sodium nitrite or the like.

An apparatus and method in accordance with the invention may be used for a variety of purposes, including without limitation, disinfecting and cleaning surfaces, increasing localized circulation or vasodilation, increasing systemic circulation or vasodilation, facilitating healing and growth, dispersing biofilms, reducing inflammation, and providing analgesic benefits.

BRIEF DESCRIPTION OF THE DRAWINGS

The foregoing features of the present invention will become more fully apparent from the following description and appended claims, taken in conjunction with the accompanying drawings and experimental data. Understanding that these drawings and data depict only typical embodiments of the invention and are, therefore, not to be considered limiting of its scope, the invention will be described with additional specificity and detail through use of the accompanying drawings and data in which:

FIG. 1 is a table illustrating the design of a subject study, including placement, descriptor, and amounts of relevant topical mixtures;

FIG. 2 is a table illustrating the percentage change in the peripheral perfusion index for the subject study in FIG. 1.

DETAILED DESCRIPTION OF THE PREFERRED EMBODIMENT

Figure 3:
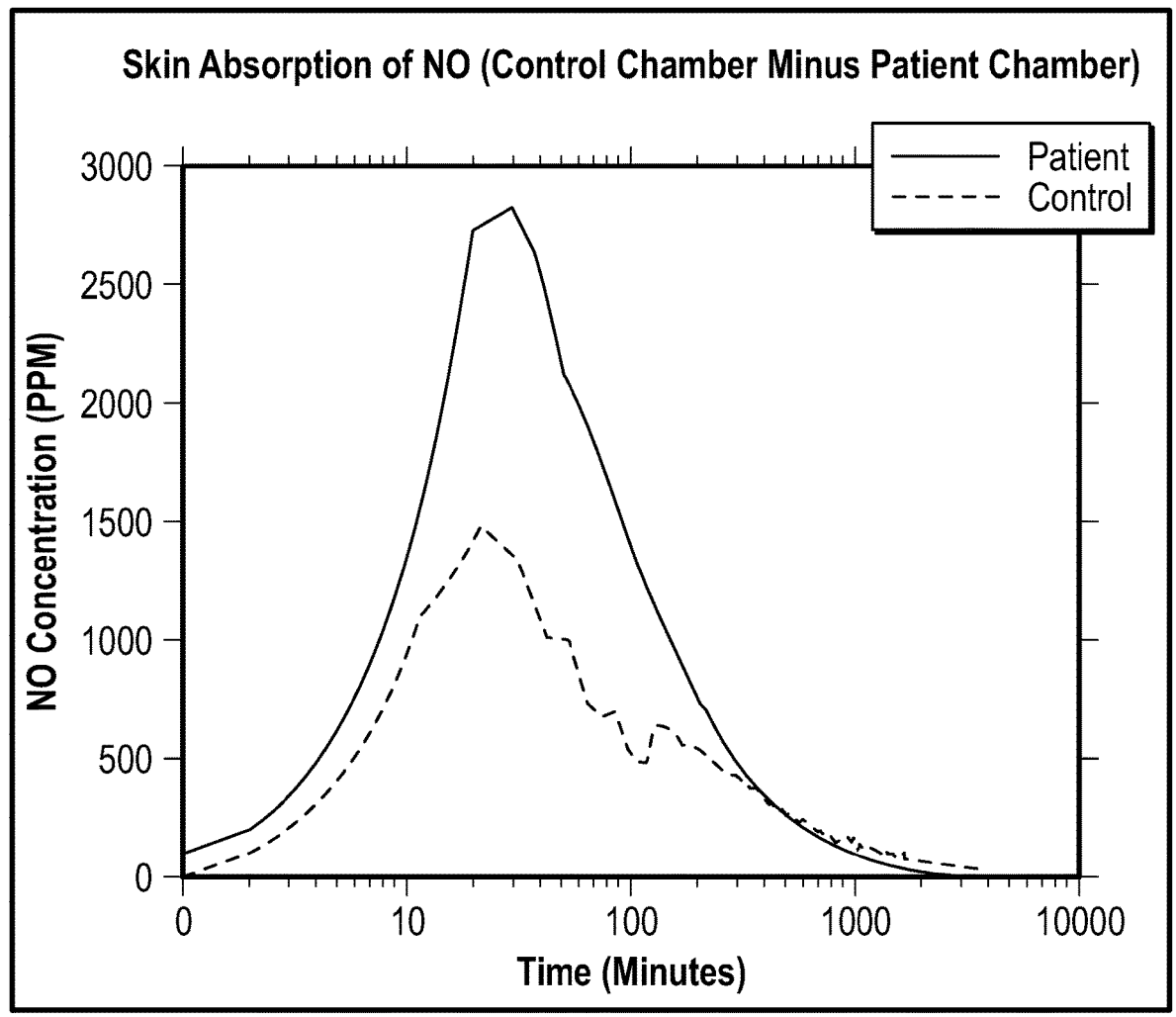
FIG. 3 is a graph comparing the production of nitric oxide in a closed, control chamber with the absorption of nitric oxide through a subject's skin.

It will be readily understood that the components and steps of the present invention, as generally described and illustrated herein, could be arranged and designed in a wide variety of different configurations. Thus, the following more detailed description of the embodiments of the system and method of the present invention, as may also be represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

The blood vessel of a mammal is generally lined with endothelial cells. These endothelial cells line the interior of the blood vessel. The blood vessel may have smooth muscle around it. The endothelial cells lining the interior of a blood vessel may include the enzyme endothelial nitric oxide synthase. The amino acid Arginine (the L-form of Arginine) may be absorbed from the gastrointestinal tract and go into the endothelial cells. The L-Arginine is then converted to nitric oxide by the endothelial nitric oxide synthase. The nitric oxide causes the blood vessel to open up, or vasodilation, resulting from relaxation of the smooth muscle cells within the blood vessel walls (particularly in large arteries, arterioles, and large veins).

Some nitric oxide also enters the blood stream and binds to the red blood cells, or hemoglobin. The binding of nitric oxide to hemoglobin results in methemoglobin.

Methemoglobin has a reduced ability to release oxygen to body tissues. Some methemoglobin in the blood stream is normal and not dangerous (generally less than 1 % of hemoglobin). Too much methemoglobin can result in methemoglobinemia and even death.

The body is able to metabolize methemoglobin. The nitric oxide may be removed from the hemoglobin and kept in the red blood cell for later use. Nitric oxide has a short half-life of a few seconds in the blood unless it is bound within a red blood cell. When a blood vessel constricts, methemoglobin may release its nitric oxide to promote vasodilation.

Nitric oxide may cause a number or tissue responses. Nitric oxide can reduce vascular smooth muscle tone. Nitric oxide can inhibit smooth muscle proliferation and migration. Nitric oxide can promote endothelial survival and repair. Nitric oxide can inhibit platelet adhesion and aggregation. Nitric oxide can inhibit inflammatory mediators.

One method for measuring vasodilation is to monitor the perfusion index, or blood flow. Perfusion index is a relative assessment of the blood pulse strength at the monitoring site in pulse oximetry. If the perfusion index trends up, it indicates vasodilation and improved peripheral perfusion, or tissue blood flow. If the perfusion index trends down, it indicates a decrease in peripheral perfusion. The perfusion index (PI) may be expressed as a rate of inflow pulsatile arterial light absorbed (AC) divided by the non-pulsatile absorbed light, venous and non-pulsatile blood or tissue (DC). PI=AC/DC.

A person may obtain the benefits of nitric oxide therapy by utilizing a topical application that generates nitric oxide. The nitric oxide may affect the surface to which the topical application is applied, and may be absorbed by a surface such as skin and affect subcutaneous tissues.

Moreover, the topical applications that may be applied can be greatly varied. The concentrations of the respective reactants, nitrites and reducing agents, can be varied and adjusted according to the intended or targeted amount of nitric oxide to be produced. The viscosity of the respective, separate, initial media can vary. Generally, applications with thinner viscosities will produce a burst of nitric oxide, but not a very prolonged production of nitric oxide. Increasing the viscosity of the separate media, and the resultant topical application, can prolong and slow the production of nitric oxide, even to the point of virtually stopping the reaction.

The viscosity of topical mixtures, and the respective, separate mediums, can vary from serums, to gels, to thixotropic substances, to any degree of viscosity desired or intended for a specific use.

The production of nitric oxide may also be prolonged by inhibiting the nitric oxide reaction on a chemical level. For example, a salt buffer may be added to one of the separate, initial media. The salt buffer may be any suitable salt, such as sodium chloride, calcium chloride, or the like. In appropriate amounts, the salt buffer acts as a competitor with the nitric oxide reactants. This can result in prolonging the production of nitric oxide without increasing the viscosity of the separate, initial media, or the resultant topical application mixture.

In one embodiment, two individual, separate, component media are provided. The first medium is a nitrite medium and generally provides the nitrite reactants in a suitable form, such as sodium nitrite, potassium nitrite, or the like. The second medium is an acidified medium and generally provides at least one acidic reactant in a suitable form, such as citric acid, lactic acid, ascorbic acid, phytic acid, acetic acid, or the like. Reaction rate and pH control are best achieved by using a mixture of multiple food-grade acids. When approximately equal amounts of the two individual components (media) are combined into a topical mixture, a reaction is initiated that produces nitric oxide.

Two separate containers may be provided, each container is capable of dispensing a suitable amount of a given medium (one of the two to be mixed). The containers may be identical in structure and composition, but need not necessarily be so. The containers may dispense the medium by a pump action, such as is common with lotions and soaps. The containers may dispense the medium by a squeezing or shaking action, such as is common with viscous or thixotropic shampoos, condiments, colloidal suspensions, gels, and other compositions.

The medium may be any suitable medium for containing and dispensing the reactants, for example, the medium may be a gel, a serum, a lotion, or a facial mud. A gel may be obtained by including a water-soluble polymer, such as methyl cellulose available as Methocel™, in a suitable solution. A serum may be obtained by including polyacrylate in a suitable solution. A lotion used to suspend the reactants for a nitrite lotion medium and an acidified lotion medium may be selected such as the Jergens® brand hand and body lotion. A facial mud may be used to suspend the reactants, for example, a facial mud medium and an acidified mud medium may be combined to produce a facial mud topical mixture. For best results, the media holding a matched pair of reactants should be essentially the same. The chemical characteristics of the media may not be strictly identical, but the physical compositions should be essentially the same so as to mix readily and not inhibit the reaction.

For example, a nitrite gel medium may have a slightly acidic to neutral pH while an acidified gel medium may have a more acidic pH than the corresponding nitrite gel medium. Using a nitrite gel medium with an acidified lotion medium may not provide optimal results.

Using different media may not provide the best rates for desired results, but would probably not be harmful or dangerous.

Generally, a topical application of nitric oxide may be provided by mixing equal amounts of a nitrite medium and an acidified medium. The topical mixture is then applied to the intended surface. The mixture may be applied to a person's healthy skin, or an open wound.

In one embodiment, a nitrite medium and an acidified medium are combined to initiate the production of nitric oxide and the combination is placed on a user's skin. The nitric oxide contacts the surface of the skin and is absorbed transdermally. Thus, nitric oxide therapy can be applied locally for a wide variety of applications. Also, local application of the nitric oxide therapy can provide a prolonged, systemic effect.

The topical mixture provides nitric oxide to the intended surface. As the nitrite medium is mixed with the acidified medium, the reduction of nitrite by the acid(s) leads to the release of nitric oxide. The exposure to nitric oxide may serve a variety of purposes.

A topical mixture that produces nitric oxide may be used for antimicrobial, antifungal, or similar cleaning purposes. Infectious diseases are caused by pathogens such as bacteria, viruses, and fungi. Antibacterial soaps can kill some bacteria, but not necessarily all bacteria. A topical mixture as described has been shown to kill as many as, and more, bacteria compared to commercially available antibacterial soaps or hospital-based instant hand antiseptics.

The nitrite medium may be formulated in any suitable medium and the concentration of reactants can be adjusted as desired as long as the intended reaction and sufficient concentrations of nitric oxide is obtained. For example, a suitable tank may be charged with distilled/deionized water (94.94% w/w) at room temperature (20"-25° C.). Sodium nitrite (3.00% w/w) and Kathan CG (0.05% w/w) may be dissolved in the water. Methocel™ (HPMC, cold dispersable; 1.75% w/w) may be stirred into the water until no lumps are present. Sodium hydroxide (ION to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Citric acid (crystalline; 0.08% w/w) may be added to adjust the mixture to a pH of 6.0. Small quantities of sodium hydroxide may be used to adjust the pH as needed. The individual percentages may be adjusted as desired for the best results.

In a separate embodiment, a nitrite medium may be formulated as follows: water, 94.8945%; sodium nitrite, 3.0000%; hydroxypropyl methylcellulose, 1.0000%; phenoxyethanol, 0.4500%; caprylyl glycol, 0.2500%; ethylhexylglycerin, 0.1500%; hexylene glycol, 0.1500%; tetrasodium EDTA, 0.1000%; butylene glycol, 0.0015%; grape (vitis vinifera) seed extract, 0.0010%; Camellia Sinensis leaf extract, 0.0010%; panax ginseng root extract, 0.0010%; and chamomilla recutita (matricaria) flower extract, 0.0010%.

In a separate embodiment, a nitrite medium may be formulated as follows: water, 74%; caprylic/capric triglyceride, 10%; sodium acrylate/acryloyldimethyltaurate/dimethylacrylamide crosspolymer, isohexadecane, polysorbate 60, 5%; cetearyl alcohol, 4%; sodium nitrite, 3%; algae extract, Artemisia vulgaris extract, 3%; and phenoxyethanol, caprylyl glycol, ethylhexyglycerin, hexylene glycol, 1%.

In a separate embodiment, a nitrite medium may be formulated as follows: water, 93.1430%; sodium nitrite, 3.0000%; sodium bicarbonate, 1.7500%; hydroxypropyl methylcellulose, 1.0000%; phenoxyethanol, 0.4500%; caprylyl glycol, 0.2500%; ethylhexylglycerin, 0.1500%; hexylene glycol, 0.1500%; tetrasodium EDTA, 0.1000%; butylene glycol, 0.0015%; glycerin, 0.0015%; moms alba root extract, 0.0010%; serenoa serrulata fruit extract, 0.0010%; Rosmarinus Officinalis (rosemary) leaf extract, 0.0010%; and Urtica Dioica (nettle) extract, 0.0010%.

In a separate embodiment, a nitrite medium may be formulated as follows: water, 87.1470%; sodium nitrite, 9.0000%; sodium bicarbonate, 1.7500%; hydroxypropyl methylcellulose, 1.0000%; phenoxyethanol, 0.4500%; caprylyl glycol, 0.2500%; ethylhexylglycerin, 0.1500%; hexylene glycol, 0.1500%; tetrasodium EDTA, 0.1000%; butylene glycol, 0.0015%; glycerin, 0.0015%; moms alba root extract, 0.0010%; serenoa serrulata fruit extract, 0.0010%; Rosmarinus Officinalis (rosemary) leaf extract, 0.0010%; and Urtica Dioica (nettle) extract, 0.0010%. This formulation for the nitrite medium was used for the gel labeled "C" in FIG. 1.

In a separate embodiment, a nitrite medium may include appropriate percentages of the following: water; glycerin; glyceryl stearate, cetearyl alcohol, sodium stearoyl lactylate; sodium nitrite; santalum album (sandalwood) wood extract, phellodendrom amurense bark extract, hordeum distichion (barley) extract; algae extract, Artemisia vulgaris extract; cetearyl alcohol; sodium acrylate/acryloyldimethyltaurate/dimethylacrylamide crosspolymer, isohexadecane, polysorbate 60; phenoxyethanol, caprylyl glycol, ethylhexylglycerin, hexylene glycol; cetyl esters; cyclopentasiloxane; hydrolyzed align, Chlorella Vulgaris extract, sea water, water; dimethicone; capric/caprylic triglycerides, linoleic acid, soy sterols, soy phospholipids; Olea Europaea (olive) fruit unsaponifiables; xanthan gum; tocopheryl acetate; and hyaluronic acid.

In a separate embodiment, a nitrite medium may include appropriate percentages of the following: water; glyceryl stearate, cetearyl alcohol, sodium stearoyl, lactylate; sodium nitrite; cetearyl alcohol; cety esters; cyclopentasiloxane; and dimethicone.

The acidified medium may be formulated in any suitable carrier and the concentration of the reactants can be adjusted as desired as long as the intended reaction and sufficient concentrations of nitric oxide are obtained. For example, a suitable tank may be charged with distilled/deionized water (89.02% w/w) at room temperature (20"-25° C.). Kathan CG (0.05% w/w) may be dissolved in the water. Methocel™ (HPMC, cold dispersable; 1.75% w/w) may be stirred into the water until no lumps are present. Sodium hydroxide (ION to approximately pH 8; 0.09% w/w) may be rapidly stirred into the water to thicken, and care should be taken to avoid trapping air bubbles that can occur as a result of higher shear mixing.

EDTA, Na4 salt (0.10% w/w) may be stirred into the water until dissolved. Stirring may continue until the Methocel™ is completely hydrated. Lactic acid (85% liquid solution; 3.00% w/w) and ascorbic acid (USP, crystalline; 3.00% w/w) may be stirred in until completely dissolved. Citric acid (crystalline; 3.00% w/w) may be added to adjust the mixture to a pH of 6.0. Small quantities of sodium hydroxide may be used to adjust the pH as needed. The individual percentages may be adjusted as desired for the best results.

In a separate embodiment, an acidified medium may be formulated as follows: water, 90.4695%; lactic acid, 5.0000%; citric acid, 2.500%; hydroxypropyl methylcellulose (or polyacrylate crosspolymer-6), 1.400%; phenoxyethanol, 0.2250%; caprylyl glycol, 0.1250%; tetrasodium EDTA, 0.1000%; ethylhexylglycerin, 0.0750%; hexylene glycol, 0.0750%; sodium hydroxide, 0.0250%; butylene glycol, 0.0015%; grape (Vitis Vinifera) seed extract, 0.0010%; Camellia Sinensis leaf extract, 0.0010%; panax ginseng root extract, 0.0010%; and chamomilla recutita (matricaria) flower extract, 0.0010%.

In a separate embodiment, an acidified medium may be formulated as follows: water, 88.2695%; lactic acid, 5.0000%; citric acid, 3.5000%; glycerin, 1.5750%; hydroxypropyl methylcellulose, 1.0000%; phenoxyethanol, 0.2250%; caprylyl glycol, 0.1250%; tetrasodium EDTA, 0.1000%; ethylhexylglycerin, 0.0750%; hexylene glycol, 0.0750%; sodium hydroxide, 0.0250%; hydroxypropyl cyclodextrin, 0.0200%; palmitoyl tripeptide-38, 0.0050%; butylene glycol, 0.0015%; moms alba root extract, 0.0010%; serenoa serrulata fmit extract, 0.0010%; Rosmarinus Officinalis (rosemary) leaf extract, 0.0010%; and uritica dioica (nettle) extract, 0.0010%.

In a separate embodiment, an acidified medium may be formulated as follows: water, 84.7735%, lactic acid, 7.0000%; citric acid, 5.0000%; glycerin, 1.5750%; hydroxypropyl methylcellulose, 1.0000%; phenoxyethanol, 0.2250%; caprylyl glycol, 0.1250%; tetrasodium EDTA, 0.1000%; ethylhexylglycerin, 0.0750%; hexylene glycol, 0.0750%; sodium hydroxide, 0.0250%; hydroxypropyl cyclodextrin, 0.0200%; palmitoyl tripeptide-38, 0.0050%; and butylene glycol, 0.0015%. This formulation for the acidified medium was used for the gel labeled "C" in FIG. 1.

In a separate embodiment, each medium may include appropriate amounts of the respective reactants and appropriate percentages of the following: water; glycerin; cellulose gum; celery juice extract; algae extract, Artemisia vulgaris extract; and phenoxyethanol, caprylyl glycol, ethylhexylglycerin, hexylene glycol.

Ranges of acceptable constituents for each medium may include plus or minus 15% with respect to any constituent.

The use of at least two acids in producing the acidified medium may improve the shelf life of the acidified medium. Generally maintaining a pH of from about 3 to about 5 or above (so long as not too caustic for skin) has been found very useful in maintaining the shelf life of the product.

A topical mixture that produces nitric oxide has been shown to be effective in cleaning and disinfecting hands. For example, three sets of volunteers, with approximately 26 people in each set, participated in a test to determine the effectiveness of nitric oxide as a cleaning and disinfecting agent. The right and left hands of each person in each set of volunteers were swabbed with cotton-tipped applicators prior to any type of washing. The applicators were plated onto nutrient blood agar petri dishes using the three corner dilution method.

Each set of volunteers washed their hands using separate soaps for washing. The first set of volunteers washed their hands for thirty (30) seconds using a topical mixture of equal parts of nitrite gel medium and acidified gel medium as described herein above. The second set of volunteers washed their hands for thirty (30) seconds using a commercial anti-bacterial agent Avagard™D. The third set of volunteers washed their hands for fifteen (15) seconds using Dial™ Complete Foaming Hand Wash, and then rinsed for fifteen (15) seconds and dried.

The right and left hands of each person in each set of volunteers were swabbed again with cotton-tipped applicators after washing. The applicators were plated onto nutrient blood agar petri dishes using the three corner dilution method. All the blood agar petri dishes were incubated for forty-eight (48) hours at 35° C. The results were tabulated based on a grading scale of bacteria colonization. The testing showed that a topical mixture that produces nitric oxide reduced the relative bacterial content by approximately 62%. Avagard™D reduced the relative bacterial content by approximately 75%. Dial™ Complete Foaming Hand Wash reduced the relative bacterial content by approximately 33%. Thus, a topical mixture that produces nitric oxide was found to be approximately twice as effective at cleaning and disinfecting hands than Dial™ Complete Foaming Hand Wash and almost as effective as Avagard™D.

It has been determined that the dose required to kill bacteria on a surface, such as a person's skin, is at least approximately 320 ppm of nitric oxide. A topical gel mixture of approximately three (3) grams of nitrite gel medium and approximately three (3) grams of acidified gel medium that produces nitric oxide has been shown to deliver approximately 840 ppm of nitric oxide. Similarly, a topical gel mixture of approximately three (3) grams of nitrite lotion medium and approximately three (3) grams of acidified lotion medium that produces nitric oxide has been shown to deliver approximately 450 ppm of nitric oxide.

A topical mixture that produces an effective amount of nitric oxide has been shown to be effective in promoting vasodilation in generally healthy individuals, including systemic vasodilation. Varying amounts of a topical mixture of gel mediums were applied to the healthy skin of various individuals. Gels used to evaluate transdermal absorption of nitric oxide and promotion of vasodilation were formulated in varying viscosities or thicknesses, and with varying concentrations of the nitric oxide reactants. Thus, the possible amount of nitric oxide that could be produced was varied between the separate topical mixtures, and the production of nitric oxide was evaluated depending on the viscosities of the gels.

It was determined that the viscosity of the gels used to form the topical mixture should be optimized to provide a lasting, prolonged production of nitric oxide and promote transdermal absorption of nitric oxide. As noted in FIG. 1, Study 8 utilized Gel A (the most viscous gel), but the production of nitric oxide was noticeably slowed unless the application site was kept "wet." The process of keeping the site wet diluted Gel A, lowering the viscosity, but also promoted production of nitric oxide. Thus, a topical mixture that was too viscous would dry out and decrease or stop the production of nitric oxide. Also, a topical mixture that was too thin having little viscosity would provide only a short burst production of nitric oxide and not enough transdermal absorption of nitric oxide.

Specifically, topical mixtures identified as A, B and C were used in the experimentation. The nitrite gel medium and the reducing agent or acidified medium for each topical mixture contained varying amounts of reactants. Likewise, the viscosities of the gels were varied. The viscosity of the topical mixtures A, B and C proceed from highest to lowest, with A being the most viscous and C being the least viscous. The site and amount of the respective gels applied to each study, or person, is shown in FIG. 1.

Hemodynamic measurements for each study were recorded at 30 minutes and 15 minutes prior to application of the respective gels. Hemodynamic measurements for each study were recorded again at 5, 15, 30, 45, 60, 75, 90, and 120 minutes after application of the respective gels.

For example, Table I below shows the hemodynamic changes for Study 10 with respect to systolic pressure, diastolic pressure, mean arterial blood pressure (MABP), and heart rate.

TABLE I

|  | Systolic Pressure | Diastolic Pressure | MABP | HR |
|---|---|---|---|---|
| Pre 30 mins. | 130 | 80 | 113 | 75 |
| Pre 15 mins. | 132 | 81 | 115 | 76 |
| Post 5 mins. | 130 | 78 | 113 | 78 |
| Post 15 mins. | 128 | 76 | 111 | 72 |
| Post 30 mins. | 122 | 70 | 105 | 68 |
| Post 45 mins. | 115 | 69 | 100 | 70 |
| Post 60 mins. | 112 | 67 | 97 | 64 |
| Post 75 mins. | 120 | 70 | 103 | 70 |
| Post 90 mins. | 115 | 68 | 99 | 68 |
| Post 120 mins. | 119 | 70 | 103 | 69 |

Table 2 below shows the Peripheral Perfusion Index (PI) for Study 10.

TABLE 2

|  | PI |
|---|---|
| Pre 30 mins. | 4.0 |
| Pre 15 mins. | 3.8 |
| Post 5 mins. | 4.2 |
| Post 15 mins. | 6.0 |
| Post 30 mins. | 7.0 |
| Post 45 mins. | 7.8 |
| Post 60 mins. | 9.0 |
| Post 75 mins. | 6.0 |
| Post 90 mins. | 8.0 |
| Post 120 mins. | 7.0 |

Table 3 below shows the methemoglobin (metHg) percentages for Study 10.

TABLE 3

|  | metHg % |
|---|---|
| Pre 30 mins. | 0.2 |
| Pre 15 mins. | 0.2 |
| Post 5 mins. | 0.3 |
| Post 15 mins. | 0.5 |
| Post 30 mins. | 0.5 |
| Post 45 mins. | 0.5 |
| Post 60 mins. | 0.5 |
| Post 75 mins. | 0.5 |
| Post 90 mins. | 0.5 |
| Post 120 mins. | 0.5 |

To ensure that methemoglobin was not "pulling" or gathering in a localized area of the body, methemoglobin percentage was measured from the middle finger, index finger, and thumb of the subject's right and left hands, and from the middle toe, second toe, and big toe of the subject's right and left feet prior to the application of the topical mixture and one hour after application of the topical mixture that produced nitric oxide. No significant pulling was found. The results are provided in Table 4 below.

TABLE 4

|  | metHg % (prior) | metHg % (one hour) |
|---|---|---|
| Lefthand, Middle finger | 0.2 | 0.5 |
| Lefthand, Index finger | 0.2 | 0.5 |
| Lefthand, Thumb | 0.0 | 0.4 |
| Right hand, Middle finger | 0.0 | 0.5 |
| Right hand, Index finger | 0.0 | 0.5 |
| Right hand, Thumb | 0.0 | 0.5 |
| Left foot, Middle toe | 0.2 | 0.5 |
| Left foot, Second toe | 0.2 | 0.4 |
| Left foot, Big toe. | 0.1 | 0.5 |
| Right foot, Middle toe | 0.0 | 0.4 |
| Right foot, Second toe | 0.0 | 0.4 |
| Right foot, Big toe. | 0.0 | 0.4 |

As shown in FIG. 2, the change in peripheral perfusion index across all studies shows that a topical mixture that produces an effective amount of nitric oxide increases vasodilation systemically. Also, a topical mixture that produces nitric oxide more quickly may have less sustained systemic effects. A topical mixture that produces nitric oxide over a more prolonged period of time can have sustained hemodynamic, systemic effects for up to two hours. The methemoglobin levels were consistent throughout the body demonstrating a whole body distribution of nitric oxide, while maintaining acceptable levels of methemoglobin.

The kinetics for the formation of nitric oxide were also evaluated to determine if nitric oxide was absorbed better through some skin areas as compared to other. For example, Table 5 below shows the nitric oxide production comparison between a "control" amount of gel A (production of nitric oxide in a closed container) and the production of nitric oxide using the same amount of gel A applied to the chest of Study 4.

TABLE 5

|  | Control-NO (ppm) | Chest-NO (ppm) |
|---|---|---|
| 0 mins. | 740 | 0 |
| 7 mins. | 756 | 0 |
| 13 mins. | 500 | 156 |
| 23 mins. | 352 | 58 |
| 34 mins. | 104 | 26 |
| 45 mins. | 21 | 2 |

As another example, Table 6 below shows the nitric oxide production comparison between a "control" amount of gel A (production of nitric oxide in a closed container) and the production of nitric oxide using the same amount of gel A applied to the right leg of Study 5.

TABLE 6

|  | Control-NO (ppm) | Chest-NO (ppm) |
|---|---|---|
| 0 mins. | 877 | 34 |
| 8 mins. | 150 | 10 |
| 17 mins. | 101 | 6 |
| 30 mins. | 82 | 4 |
| 37 mins. | 40 | 5 |
| 40 mins. | 37 | 5 |
| 55 mins. | 12 | 4 |
| 65 mins. | 17 | 1 |
| 97 mins. | 10 | 0 |

As shown in FIG. 3, and as substantiated by the data in Tables 5 and 6, nitric oxide produced from application of a topical mixture is absorbed through the skin of a person. As established from the other data from FIG. 2 and Tables 1-4, the nitric oxide absorbed through the skin promotes systemic vasodilation without substantial risk of methemoglobinemia.

The topical mixture applied to a given site would dry out approximately 30 minutes after application, but the hemodynamic effects could still be measured for approximately an additional 60 to 90 minutes.

The skin may be covered with a barrier, cover, or bandage after application of the nitric oxide producing topical mixture. Such a barrier can serve many purposes, including, maintaining the moisture content in the topical mixture, preventing debris or contaminants from getting into the topical mixture or on the skin, and promoting the transdermal absorption of the nitric oxide produced.

The amount of nitric oxide that is produced and absorbed transdermally may vary based on site applications, and certainly varies depending on the amount of nitric oxide producing reactants present in the topical mixture applied and the duration of the nitric oxide producing reaction. Generally, the amount of nitric oxide absorbed transdermally between initial application of the topical mixture and approximately 60-90 minutes is between approximately 1000 ppm and 2000 ppm, and can be between 500 ppm and 2500 ppm.

One possible application for this data is in the treatment of peripheral artery disease (PAD). Peripheral artery disease is a common disorder with a progressive reduction in lower limb blood flow, which in severe cases leads to chronic pain, gangrene, and eventually limb loss. Peripheral artery disease is characterized by progressive occlusion of large and medium-sized arteries outside the cardio-pulmonary and cerebral vascular systems. Dysregulation of nitric oxide production in the endothelial lining of blood vessels is felt to be a major contributor.

Application of topical mixtures that produce nitric oxide may become a less expensive and faster mechanism to improve bioavailability of systemic nitric oxide pools as compared to currently available treatments.

Likewise, application of topical mixtures that produce nitric oxide may become a therapeutic possibility in the treatment of systemic hemodynamic disorders of all kinds.

A mixture that produces nitric oxide may be used for a variety of purposes and ailments, including without limitation, diabetic and non-healing wounds or lesions, leprosy, tuberculosis, malaria, anti-parasitic uses, etc. In one embodiment, the mixture can be used as a topical application on healthy skin. There are combinations of uses also possible.

A topical mixture that produces nitric oxide may be used to help heal various kinds of wounds. Tests have been performed wherein a topical mixture that produces nitric oxide as described herein is applied regularly to an open wound that is generally resistant to healing. The wound was seen to show significant healing within a few weeks.

For example, a person in Canada had poor circulation and unresponsive diabetic ulcers on the person's feet. The person was immobilized and in a wheel chair, and had been scheduled for amputation to remove the person's foot about a month after this experiment began. A topical mixture that produces nitric oxide was applied to the diabetic ulcers once a day. The person soaked the effected foot in a footbath solution that produces nitric oxide for approximately twenty minutes once every four days. Within two weeks the person was able to walk and go out in public. Within 4-6 weeks, the person was mobile and had achieved a substantially complete recovery. Meanwhile, the scheduled amputation was cancelled.

The nitric oxide may promote the healing of diabetic ulcers in at least two ways: the surface of the wound area is cleaned and sterilized, and the underlying vascularization of the area is improved, vasodilation. The nitric oxide may also help disperse any biofilms created as a result of the diabetic ulcer. Thus, healing of the wound is promoted from the surface and below the surface.

A topical mixture that produces nitric oxide may be used for localized analgesic purposes. The analgesic effect nitric oxide may be provided via topical application.

A topical mixture that produces nitric oxide may be used for treating erectile dysfunction. Nitric oxide acts as a vasodilator. The nitric oxide provided by the topical mixture and absorbed transdermally may stimulate and increase blood flow to the treated area. Increased blood flow may also help performance of muscles or muscle groups that receive nitric oxide transdermally.

A topical mixture that produces nitric oxide may be used for anti-inflammatory purposes.

A topical mixture that produces nitric oxide may also be used to disperse a biofilm. Acne is an example of a biofilm. Biofilms are colonies of dissimilar organisms that seem to join symbiotically to resist attack from antibiotics. Nitric oxide signals a biofilm to disperse so antibiotics can penetrate the biofilm. It is also believed that nitric oxide interferes with the uptake of iron.

It has been shown that a topical mixture that produces nitric oxide will also treat acne. Acne is a biofilm. As an example, at least two people had a considerable amount of acne on their faces. A topical mixture that produces nitric oxide was applied to the acne twice a day. Within two days a marked amount of the acne had been cleared and inflammation was greatly reduced. Within two weeks the acne was substantially gone. A topical mixture that produces nitric oxide will treat the surface of the acne, as well as treating the underlying causes of the acne. The resultant nitric oxide will disperse the biofilm, act as an antiseptic microbicide agent against bacteria, and promote vascularization subcutaneously to promote cleansing and healing.

Other types of biofilms can include methicillin-resistant Staphylococcus aureus (MRSA) and gangrene. For example, two people had unresponsive, non-healing wounds on their lower legs, including biofilms that further prevented healing. A topical mixture that produces nitric oxide was applied to the wounds twice a day. The person soaked and washed the effected wound in a bath solution that produces nitric oxide for approximately twenty minutes once every three to four days. Within approximately four weeks the wound had closed and the person had achieved a substantially complete recovery.

A topical mixture that produces nitric oxide can treat the surface of the skin and help promote healing, but demonstrating how to effectively promote vasodilation via transdermal absorption of nitric oxide shows that the underlying, subcutaneous issues preventing healing can also be treated. The nitric oxide absorbed transdermally can act subcutaneously to disperse a biofilm, act as an antiseptic microbicide agent against bacteria, reduce or eliminate inflammation, and promote vascularization subcutaneously to promote cleansing and healing.

It was shown that a topical mixture that produces nitric oxide will kill squamous cells, pre-cancerous cells, if the concentration of nitric oxide is high enough. Tests intending to show that a topical mixture that produces nitric oxide would grow hair based in part on the increase of blood flow that accompanies application of nitric oxide actually showed that nitric oxide in as high doses provided as described herein above did kill squamous cells.

A topical mixture that produces nitric oxide may be used for more cosmetic purposes. The nitric oxide dose provided via topical application may reduce the appearance of wrinkles.

A variety of topical mixtures may be obtained by combining one of various types of nitrite mediums with one of various types of acidified mediums. For example and without limitation, a nitrite gel medium may be combined with an acidified serum medium, or vice versa. Likewise, other combinations of mediums are possible.

It may also be noticed that using nitric oxide producing gels as a technique to wash and sterilize hands over a significant number of days may lead to vasodilation of the blood vessels in the hands.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

The invention claimed is:

1. A method for manufacturing a product to increase systemic vasodilation, comprising:
   producing a first topical medium comprising a nitrite compound, wherein the first topical medium is configured on reaction to release an amount of nitric oxide topically to increase the systemic vasodilation of a recipient;
   producing a second topical medium comprising one or more reducing agents, wherein the second topical medium is configured on reaction to release an amount of nitric oxide topically to increase the systemic vasodilation of the recipient;
   packaging the first and second topical mediums in a kit such that the first and second topical mediums are adapted to be mixed by a user to initiate production of nitric oxide and configured on reaction to be applied topically to the recipient to supply nitric oxide for absorption transdermally such that the systemic vasodilation of the bloodstream of the recipient will increase as compared to an initial vasodilation at the time of initial application.

2. The method of claim 1, wherein the first topical medium comprises sodium nitrite.

3. The method of claim 1, wherein the first topical medium further includes at least one salt selected from a group consisting of sodium chloride and calcium chloride.

4. The method of claim 1, wherein the second topical medium further includes at least one salt selected from a group consisting of sodium chloride and calcium chloride.

5. The method of claim 1, further comprising providing a barrier configured to cover at least a portion of the surface after application of the mixed first and second topical mediums during use.

6. The method of claim 1, wherein the first topical medium comprises potassium nitrite.

7. The method of claim 1, wherein the second topical medium comprises at least two reducing agents selected from a group consisting of citric acid, ascorbic acid, phytic acid, acetic acid, formic acid, and lactic acid.

8. The method of claim 1, wherein at least one of the first topical medium and the second topical medium further includes a thickening agent.

9. The method of claim 1, wherein the first topical medium further comprises sodium bicarbonate.

10. A method of manufacturing a product for treating a systemic disorder comprising:
    producing a first topical medium comprising a nitrite compound, wherein the first topical medium is configured on reaction to release an amount of nitric oxide topically to increase the systemic vasodilation of a recipient;
    producing a second topical medium comprising a reducing agent, wherein the second topical medium is configured on reaction to release an amount of nitric oxide topically to increase the systemic vasodilation of the recipient;
    packaging the first and second topical mediums in a kit such that the first and second topical mediums are adapted to be mixed by a user to initiate production of nitric oxide and configured on reaction to be applied topically to the recipient to increase the systemic vasodilation of the bloodstream of the recipient relative to an initial vasodilation at the time of initial application; and
    producing a barrier provided in the kit and configured to cover at least a portion of an epidermal application surface of the recipient after application of the mixed first and second topical mediums to the epidermal application surface of the recipient during use.

11. The method of claim 10, wherein the first topical medium further comprises sodium bicarbonate.

12. The method of claim 10, wherein the second topical medium includes at least two reducing agents selected from a group consisting of citric acid, ascorbic acid, phytic acid, acetic acid, formic acid, and lactic acid.

13. The method of claim 10, wherein at least one of the first and second topical mediums further comprises a salt such that when the first and second topical mediums are mixed, the mixture includes a salt buffer concentration for prolonging the production of nitric oxide, wherein the salt used in the salt buffer includes at least one salt selected from a group consisting of sodium chloride and calcium chloride.

14. A method for manufacturing a product to increase vasodilation of a subject during application of a product treatment, comprising:
    providing a first topical medium comprising a nitrite compound, wherein the first topical medium is configured on reaction to release a dose of nitric oxide topically to increase the systemic vasodilation of a subject;
    providing a second topical medium comprising a reducing agent, wherein the second topical medium is configured on reaction to release a dose of nitric oxide topically to increase the systemic vasodilation of the subject,
    wherein at least one of the first topical medium and the second topical medium comprises at least one salt selected from a group consisting of sodium chloride and calcium chloride; and
    wherein the first topical medium and the second topical medium are configured for use such that the first topical medium and the second topical medium are mixed by a user to initiate a reaction resulting in production of nitric oxide, wherein the at least one salt is adapted to act as a salt buffer for prolonging the production of nitric oxide of the mixture, and wherein topical application of the mixture provides a treatment dose to a treatment surface of the subject whereby an effective amount of nitric oxide is administered transdermally, with the effect of increasing a systemic vasodilation of a bloodstream of the subject relative to an initial vasodilation of the subject.

15. The method of claim 14, further comprising providing a barrier configured to cover the treatment surface after application of the mixture during use.

16. The method of claim 14, wherein the first topical medium further comprises sodium bicarbonate.

17. The method of claim 14, wherein the first topical medium and the second topical medium each further include a thickening agent.

18. The method of claim 10, wherein treatment of the systemic disorder further includes providing at least one or more of an antimicrobial treatment, an anti-inflammatory treatment, and/or an antiseptic treatment.

19. The method of claim 10, wherein treatment of the systemic disorder further includes providing at least one or more of an antifungal and/or an antibacterial treatment.

20. The method of claim 10, wherein treatment of the systemic disorder further includes providing a diabetic treatment.

21. The method of claim 10, wherein treatment of the systemic disorder further includes providing a cancer treatment.

* * * * *